United States Patent

Poli et al.

[11] 4,030,887
[45] June 21, 1977

[54] CARBON MONOXIDE DETECTION APPARATUS AND METHOD

[75] Inventors: Albert A. Poli, Pittsburgh; Clayton J. Bossart, Monroeville; Thomas P. Benzie, Pittsburgh, all of Pa.

[73] Assignee: Mine Safety Appliances Company, Pittsburgh, Pa.

[22] Filed: June 18, 1976

[21] Appl. No.: 697,381

[52] U.S. Cl. .......................... 23/232 E; 23/254 E; 73/23

[51] Int. Cl.² ................. G01N 31/06; G01N 31/10

[58] Field of Search ......... 23/232 E, 232 R, 254 R, 23/254 E, 255 R, 255 E, 231 C, 230 A, 253 A; 73/23, 23.1, 25, 26, 27 R

[56] References Cited
UNITED STATES PATENTS

| | | | |
|---|---|---|---|
| 2,916,358 | 12/1959 | Valentine et al. | 23/232 E X |
| 3,300,282 | 1/1967 | Risk et al. | 23/232 R |
| 3,311,835 | 11/1963 | Jenkins | 23/232 C |
| 3,871,827 | 3/1975 | Seiler et al. | 23/232 R X |

Primary Examiner—Robert M. Reese
Attorney, Agent, or Firm—Brown, Murray, Flick & Peckham

[57] ABSTRACT

A carbon monoxide removing catalytic material is disposed in one end of a first hollow column having open ends while porous inactive material is disposed in one end of a similar second column to offer substantially the same resistance to air flow as the catalytic material. There is a bed of regenerable air-drying substance in each column between the other material therein and the opposite end of the column. The volume and resistance to air flow of the two beds is substantially the same. Valve means connect an air stream with said opposite end of the first column and simultaneously connect said end of the second column with the atmosphere. Conduit means connect the other ends of the columns with each other, with an outlet port between the columns connected with the inlet of a pressure regulator. The valve means can be reversed periodically to reverse the direction of air flow through the columns, with only part of the air stream that enters the conduit means from either column flowing to the regulator while the rest of the stream flows in reverse direction through the other column to dry the air-drying bed therein. The outlet of the pressure regulator is connected to a carbon monoxide detector, which in turn is connected with means for indicating the amount of carbon monoxide detected every time the air flow to the detector comes from said second column.

6 Claims, 2 Drawing Figures

U.S. Patent June 21, 1977 4,030,887

CARBON MONOXIDE DETECTION APPARATUS AND METHOD

It is among the objects of this invention to provide apparatus for detecting carbon monoxide in air, in which the life of the catalyst used is greatly increased, in which close temperature control is unnecessary, in which the reference used by the carbon monoxide detecting means is updated once every switching cycle, which does not require a lengthy warm-up period, and which contains fewer parts for a reduced cost than heretofore.

Figure 1:
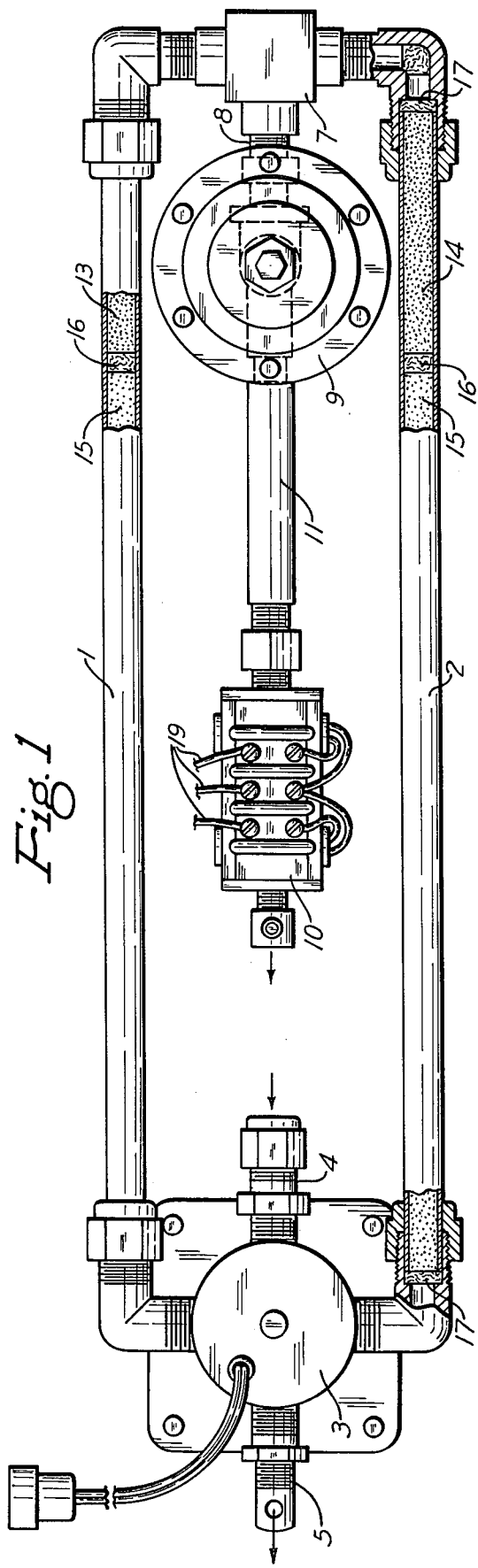
Figure 2:
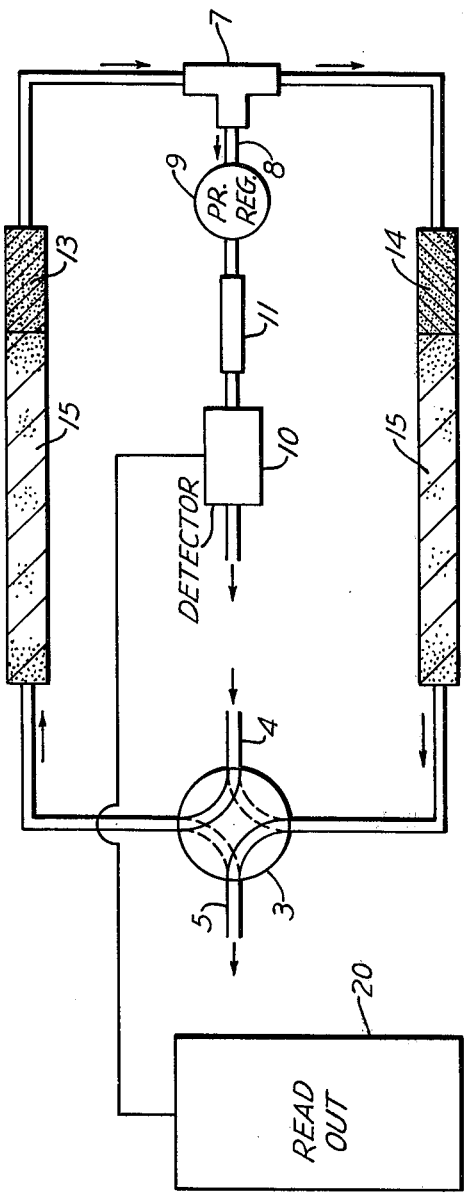

The preferred embodiment of the invention is illustrated in the accompanying drawings, in which FIG. 1 is a plan view, partly broken away in section; and FIG. 2 is a diagram depicting the circuit.

Referring to the drawings, a pair of parallel hollow columns 1 and 2 are formed from pipes, the ends of which are connected in such a manner as to form a rectangular structure. Thus, at one end the two columns are connected to oppositely disposed ports in a four-way valve 3, preferably an electrically operated solenoid valve. One of the other valve ports is connected to an inlet pipe 4, preferably between the two columns. The remaining valve port exhausts to the atmosphere through a pipe 5. In one position, as shown in FIG. 2, the valve connects its inlet with column 1 and simultaneously connects column 2 with the atmosphere. When the valve is reversed, the air flow is directed into the second column and the first column is connected with the atmosphere.

At the opposite end of the columns they are rigidly connected by a conduit including a tee 7. The tee has a central outlet port that is connected by coupling means 8 with conventional flow restricting means, such as a pressure regulator 9, the outlet of which is connected with an electrically operated carbon monoxide detector 10 of conventional form. Most suitably, the detector is the type in which carbon monoxide is oxidized by a bed of catalytic material, such as Hopcalite for example, which causes an increase in the temperature of the bed that is proportional to the carbon monoxide content of the gas. Preferably, between the pressure regulator and the detector the connecting pipe 11 contains a conventional molecular sieve. With the pressure regulator adjusted to restrict air flow through it, some of the air entering the connecting tee 7 from either column will flow straight through the tee and then in a reverse direction back through the other column.

In the end of column 1 nearest the pressure regulator there is a carbon monoxide removing catalytic material 13, such as Hopcalite for example, that will burn out the CO in the air flowing through it. In the same end of the other column there is a body of porous inactive material 14, the purpose of which is to offer substantially the same resistance to air flow as the catalytic material does. In addition, between the material just mentioned in each column and the opposite or valve end of that column there is a bed of a regenerable air-drying substance 15 that does not significantly absorb or retain carbon monoxide, such as alumina or, more desirably, silica gel for example. The volume of this material and its resistance to air flow in the two beds are substantially the same. In other words, all of the material in each column offers the same resistance to air flow as the material in the other column. The air-drying substance and the other material in each column are separated by a filter 16, with other filters 17 disposed in the opposite ends of the column.

OPERATION

In operation, a stream of air is supplied to one of the columns through the four-way valve 3. When this air flows through column 1 containing the catalytic material 13, the carbon monoxide in the air is removed. Before reaching the catalytic material the air stream will be dried by the bed 15 of silica gel or alumina. The air stream leaving this column will divide at the tee 7 and some of it will flow across to the other column and back through it and the valve to the atmosphere, as shown in FIG. 2. As the air flows through this second column, it removes moisture that the drying material therein removed from the air stream flowing through it when the valve was in its other position. The rest of the air stream leaving column 1 flows to and through the pressure regulator and the molecular sieve and then out through the carbon monoxide detector 10. This detector, of any well-known construction, is connected by cable or wires 19 to suitable carbon monoxide read-out apparatus 20 indicated in FIG. 2, of which those skilled in this art are familiar. After a period of time of predetermined duration, the valve is reversed by a timer or the like (not shown) so that the air stream entering the valve inlet 4 will now flow through the second column 2 and the inactive porous material 14 therein. Since this material will not remove carbon monoxide, the portion of the air stream that reaches the detector will cause the detector to register the pressure of carbon monoxide. The rest of the stream will flow back through column 1 and will dry the drying material therein.

The detector will compare the carbon monoxide sample reading with the zero carbon monoxide reading that preceded it and the result will be shown by the read-out apparatus. It will be seen that once each cycle, while the air stream is flowing in the direction of the arrows in FIG. 2, a new zero reference will be obtained. This makes it unnecessary to control the temperature of the air, since the signal level stability is independent of long-term zero stability. For example, an ambient temperature change of 10° C shows no noticeable change in the read-out. Also, with this system a lengthy warm-up period is unnecessary in order to get a reliable reading. Even if there has been a loss of power or other shut-down for an hour, a ten minute warm-up period is sufficient.

Drying beds such as alumina or silica gel remove not only water vapor from the air stream, but also interfering and poison material such as $H_2S$, $SO_2$ and $NH_3$. This greatly increases the life of the catalyst. Each bed is regenerated once each cycle.

The advantages of this invention are obtained with fewer parts than heretofore and, consequently, at lower cost.

According to the provisions of the patent statutes, we have explained the principle of our invention and have illustrated and described what we now consider to represent its best embodiment. However, we desire to have it understood that, within the scope of the appended claims, the invention may be practiced otherwise than as specifically illustrated and described.

We claim:

1. Apparatus for the detection of carbon monoxide in air, comprising first and second hollow columns having open ends, a carbon monoxide removing catalytic material in one end of the first column, porous inactive material in one end of the second column offering substantially the same resistance to air flow as said catalytic material, a bed of regenerable air-drying substance in each column between said material therein and the opposite end of the column, the volume and resistance to air flow of said beds in the two columns being substantially the same, valve means for connecting an air stream with said opposite end of the first column and simultaneously connecting said opposite end of the second column with the atmosphere, conduit means connecting the other ends of the columns with each other and having an outlet port between the columns, means for reversing said valve means periodically to reverse the direction of air flow through said columns, means for restricting air flow and having an inlet connected with said outlet port and having an outlet, whereby only part of said air stream entering said conduit means from either column will flow through said restricting means and the rest of the air stream will flow through in reverse direction through the other column to dry the bed of drying substance therein, a carbon monoxide detector connected with the outlet of said flow restricting means, and means for indicating the amount of carbon monoxide detected by said detector every time the air flow to the detector comes from said second column.

2. Apparatus according to claim 1, in which said air-drying substance is silica gel or alumina.

3. Apparatus according to claim 1, in which said valve means include a four-way valve rigidly connected with said opposite ends of said columns and having an inlet for said air stream and an outlet for air from either column and also having a pair of ports, said valve being provided with means for connecting either of said valve ports with said valve inlet and for simultaneously connecting the other valve port with said valve outlet, said conduit means rigidly connecting the columns at said one end, and said flow restricting means being mounted in fixed position between said conduit means and valve means.

4. Apparatus according to claim 3, in which said detector is rigidly supported by said flow restricting means between it and said valve means.

5. Apparatus according to claim 4, including a molecular sieve interposed between said flow restricting means and said detector.

6. A method of detecting carbon monoxide in air, comprising passing a stream of air through a first bed of regenerable air-drying substance and then through porous inactive material, conducting some of the dried air leaving said inactive material to a carbon monoxide detector and the rest through carbon monoxide removing catalytic material offering substantially the same resistance to air flow as said inactive material, conducting the air from said catalytic material through a second bed of regenerable air-drying substance having substantially the same volume and resistance to air flow as the first bed, exhausting the air leaving the second bed to the atmosphere, then reversing the air flow through said beds and material and conducting some of the air leaving said catalytic material to said detector while the rest of the air flows through said inactive material and the first bed to atmosphere, and indicating the amount of carbon monoxide detected by the detector every time the air flow to the detector comes from said inactive material.

* * * * *